(12) United States Patent
Chang

(10) Patent No.: US 11,202,584 B2
(45) Date of Patent: Dec. 21, 2021

(54) GAIT AID

(71) Applicant: CHANG GUNG UNIVERSITY, Taoyuan (TW)

(72) Inventor: Ya-Ju Chang, Taipei (TW)

(73) Assignee: Chang Gung University, Taoyuan (TW)

(*) Notice: Subject to any disclaimer, the term of this patent is extended or adjusted under 35 U.S.C. 154(b) by 549 days.

(21) Appl. No.: 15/669,318

(22) Filed: Aug. 4, 2017

(65) Prior Publication Data

US 2018/0035921 A1 Feb. 8, 2018

(30) Foreign Application Priority Data

Aug. 5, 2016 (TW) .................................. 105124907

(51) Int. Cl.
| | |
|---|---|
| *A61B 5/11* | (2006.01) |
| *A43B 3/00* | (2006.01) |
| *A43B 17/00* | (2006.01) |
| *A61B 5/00* | (2006.01) |

(52) U.S. Cl.
CPC ............ *A61B 5/112* (2013.01); *A43B 3/0005* (2013.01); *A43B 17/00* (2013.01); *A61B 5/486* (2013.01); *A61B 5/6802* (2013.01); *A61B 5/6807* (2013.01); *A61B 5/6829* (2013.01); *A61B 5/7275* (2013.01); *A43B 3/001* (2013.01); *A61B 2505/09* (2013.01)

(58) Field of Classification Search
CPC ... A61B 5/112; A61B 2505/09; A61B 5/6807; A61B 5/6829; A61B 5/7275; A43B 3/001
See application file for complete search history.

(56) References Cited

U.S. PATENT DOCUMENTS

| | | | |
|---|---|---|---|
| 5,575,294 A | * | 11/1996 | Perry ..................... A45B 3/00 362/102 |
| 6,830,344 B2 | | 12/2004 | Reho et al. |
| 6,836,744 B1 | | 12/2004 | Asphahani et al. |
| 2007/0130804 A1 | * | 6/2007 | Levy ................. A43B 1/0027 36/136 |

(Continued)

FOREIGN PATENT DOCUMENTS

| | | |
|---|---|---|
| CN | 105266257 A | 1/2016 |
| TW | M284258 U | 1/2006 |

(Continued)

OTHER PUBLICATIONS

Ali Saad, et al., "About detection and diagnosis of freezing of gait", IEEE, Oct. 31, 2013, pp. 117-120.

(Continued)

*Primary Examiner* — Christian Jang
*Assistant Examiner* — Karen E Toth
(74) *Attorney, Agent, or Firm* — Michael Best & Friedrich LLP

(57) ABSTRACT

A gait aid is to be disposed on a shoe, and includes a detecting module, a control circuit and a projecting module. The detecting module generates a sense output based on pressure exerted on a sole of the shoe. The control circuit generates a control signal based at least on the sense output generated by the detecting module. The projecting module is (Continued)

electrically coupled to the control circuit for receiving the control signal therefrom, and is operable, based on the control signal, to project or not to project a cueing mark.

13 Claims, 5 Drawing Sheets

(56) References Cited

U.S. PATENT DOCUMENTS

| | | | | |
|---|---|---|---|---|
| 2009/0240171 | A1* | 9/2009 | Morris Bamberg | A61B 5/1038 600/595 |
| 2013/0014790 | A1 | 1/2013 | Van Gerpen | |
| 2013/0176126 | A1* | 7/2013 | Dunham | A43B 3/0015 340/573.1 |
| 2014/0249452 | A1* | 9/2014 | Marsh | A61B 5/112 600/595 |
| 2014/0303508 | A1* | 10/2014 | Plotnik-Peleg | A61B 5/744 600/483 |
| 2016/0143562 | A1* | 5/2016 | Ashby | A61B 5/1038 600/595 |
| 2016/0310341 | A1* | 10/2016 | Yu | G09B 5/02 |
| 2017/0116869 | A1* | 4/2017 | Pape | A61H 1/0262 |

FOREIGN PATENT DOCUMENTS

| | | | |
|---|---|---|---|
| TW | M425662 U | 4/2012 | |
| TW | M465907 U | 11/2013 | |
| TW | 201503882 A | 2/2015 | |
| TW | 201532598 A | 9/2015 | |
| TW | I554266 B | 10/2016 | |
| WO | 2015189631 A1 | 12/2015 | |
| WO | WO2015189631 A4 * | 12/2015 | ............... A61H 1/02 |

OTHER PUBLICATIONS

Search Report appended to an Office Action, which was issued to Taiwanese counterpart application No. 105124907 by the TIPO dated Apr. 12, 2018, with an English translation thereof (2 pages).
Xu et al., "Fuzzy Control in Gait Pattern Classification Using Wearable Sensors" IEEE, Nov. 23, 2015, pp. 62 to 67.
Search Report appended to an Office Action, which was issued to Taiwanese counterpart Application No. 105124907 by the TIPO dated Oct. 29, 2019 (2 pages, English translation included).

* cited by examiner

GAIT AID

CROSS-REFERENCE TO RELATED APPLICATION

This application claims priority of Taiwanese Patent Application No. 105124907, filed on Aug. 5, 2016.

FIELD

The disclosure relates to gait training, and more particularly to a gait aid.

BACKGROUND

A crutch mounted with a laser source is conventionally used in gait training of a patient. The laser source emits laser light to the ground in front of the patient who is using the crutch, as an indication for the patient to step forward. The crutch is inconvenient to use. In addition, in case the patient forgets to carry the crutch, gait training cannot be conducted.

SUMMARY

Therefore, one of the objects of the disclosure is to provide a gait aid that can alleviate the drawbacks of the prior art.

One of the objects of the disclosure is to provide a gait aid that can detect a mid stance phase of a foot.

One of the objects of the disclosure is to provide a gait aid that can detect a freezing-of-gait phase of two feet.

One of the objects of the disclosure is to provide a gait aid that can selectively project a cueing mark when the freezing-of-gait phase is detected.

According to one of the embodiments of the disclosure, the gait aid is to be disposed on a shoe, and includes a detecting module, a control circuit and a projecting module. The detecting module generates a sense output based on pressure exerted on a sole of the shoe. The control circuit generates a control signal based at least on the sense output generated by the detecting module. The projecting module is electrically coupled to the control circuit for receiving the control signal therefrom, and is operable, based on the control signal, to project or not to project a cueing mark. When determining, based at least on the sense output, that the gait aid is in a projection state, the control circuit generates the control signal in such a way that the projecting module projects the cueing mark, and when otherwise, the control circuit generates the control signal in such a way that the projecting module does not project the cueing mark.

According to one of the embodiments of the disclosure, a gait aid is to be disposed on a shoe, and includes a detecting module and a control circuit. The detecting module generates a sense output based on pressure exerted on a sole of the shoe. The control circuit generates a control signal based at least on the sense output generated by the detecting module. The gait aid is operatively associated with an additional one of the gait aid that is to be disposed on another shoe. The control circuit is used to further receive, from the additional one of the gait aid, a communication output associated with pressure exerted on a sole of the another shoe, and generates the control signal based further on the communication output. When determining, based on the sense output and the communication output, that the gait aid is in a projection state, the control circuit generates the control signal in such a way that the gait aid projects a cueing mark, and when otherwise, the control circuit generates the control signal in such a way that the gait aid does not project the cueing mark.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
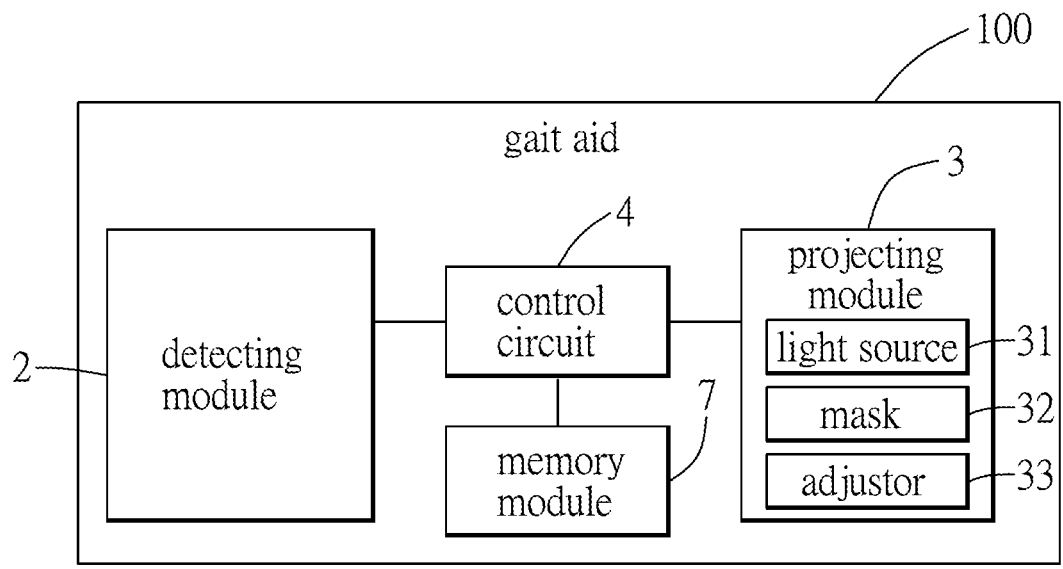
FIG. 1 is a block diagram illustrating a first embodiment of a gait aid according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
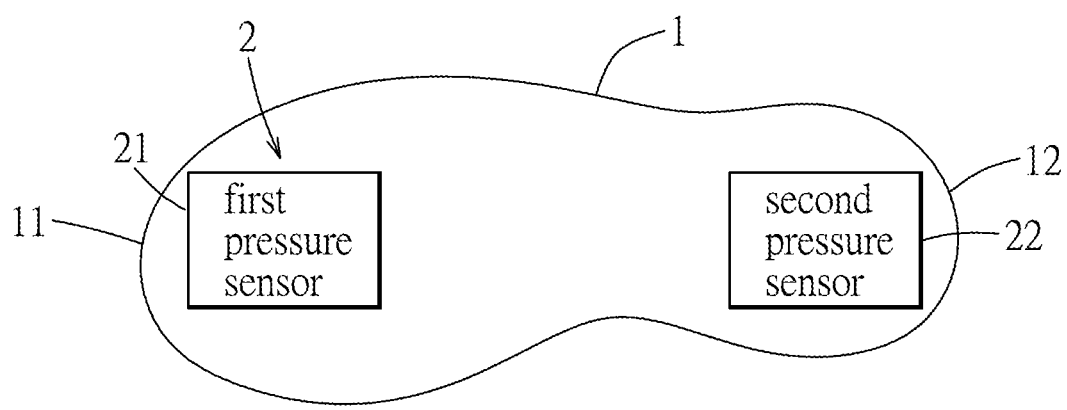
FIG. 2 is a schematic diagram illustrating a detecting module of the first embodiment.

Referring to FIGS. 1 and 2, a first embodiment of a gait aid 100 according to the disclosure is to be disposed on a shoe 1, and includes a detecting module 2, a control circuit 4, a projecting module 3 and a memory module 7 (e.g., a flash memory, a SD card, etc.).

The detecting module 2 (e.g., a pressure sensitive module) generates a sense output based on pressure exerted on a sole of the shoe 1. In this embodiment, the detecting module 2 includes a first pressure sensor 21 and a second pressure sensor 22 that are mounted on an insole. When the insole is disposed in the shoe 1, the first and second pressure sensors 21, 22 are respectively at a front portion 11 and a rear portion 12 of the shoe 1, and continuously or periodically sense the pressure exerted on the sole of the shoe 1 to respectively generate a first sense signal and a second sense signal which cooperatively serve as the sense output.

The control circuit 4 (e.g., a controller, an ASIC (application specific integrated circuit), a microprocessor, etc.) is electrically coupled to the detecting module 2 and the memory module 7, generates a control signal based at least on the sense output generated by the detecting module 2 (i.e., the first and second sense signals in this embodiment), and stores the sensed pressures respectively indicated by the first and second sense signals in the memory module 7 for future analysis. It should be noted that the control circuit 4 may be implemented in different ways. For example, it may be implemented by hardware, such as through use of an integrated circuit, or it may be implemented by software and/or firmware.

The projecting module 3 is electrically coupled to the control circuit 4 for receiving the control signal therefrom, and is operable, based on the control signal, to project or not to project a cueing mark substantially forward and downward with respect to the shoe 1. In this embodiment, the projecting module 3 includes a light source 31, a mask 32 and an adjustor 33. The light source 31 is turned on and off by the control signal, generates a light pattern with a predetermined intensity that serves as the cueing mark when turned on, and does not generate the cueing mark when turned off. The light source 31 may include, for example, a light emitting diode or a laser source. The mask 32 is formed with an adjustable aperture. The adjustor 33 may be operated to adjust the aperture, so as to prevent or allow passage of the cueing mark through the aperture, and to change the intensity of the cueing mark when the passage of the cueing mark through the aperture is allowed. In this embodiment, the cueing mark exhibits a predetermined shape (e.g., line or curve) on the ground, but the disclosure is not limited to such.

In this embodiment, the control circuit 4, the projecting module 3 and the memory module 7 are mounted on a circuit board, and the circuit board is secured to the shoe 1 by some fastening mechanism. In an example, the circuit board is formed with a plurality of eyelets, and is secured to the shoe 1 by threading laces of the shoe 1 through the eyelets thereof. In another example, the circuit board is secured to the shoe 1 by use of hook-and-loop fasteners (e.g., Velcro®).

It should be noted that, in this embodiment, the projecting module 3 is adjustable in angle with respect to the circuit board, so a distance between the cueing mark and the shoe 1 on the ground is changeable, and so the cueing mark may be projected sideways with respect to the shoe 1 (i.e., the cueing mark may be directly in front of the shoe 1 on the ground, towards the left in front of the shoe 1 on the ground, or towards the right in front of the shoe 1 on the ground).

When determining, based at least on the sense output, that the gait aid 100 is in a projection state, the control circuit 4 generates the control signal in such a way that the projecting module 3 projects the cueing mark (i.e., the light source 31 is turned on); otherwise, the control circuit 4 generates the control signal in such a way that the projecting module 3 does not project the cueing mark (i.e., the light source 31 is turned off).

Figure 3:
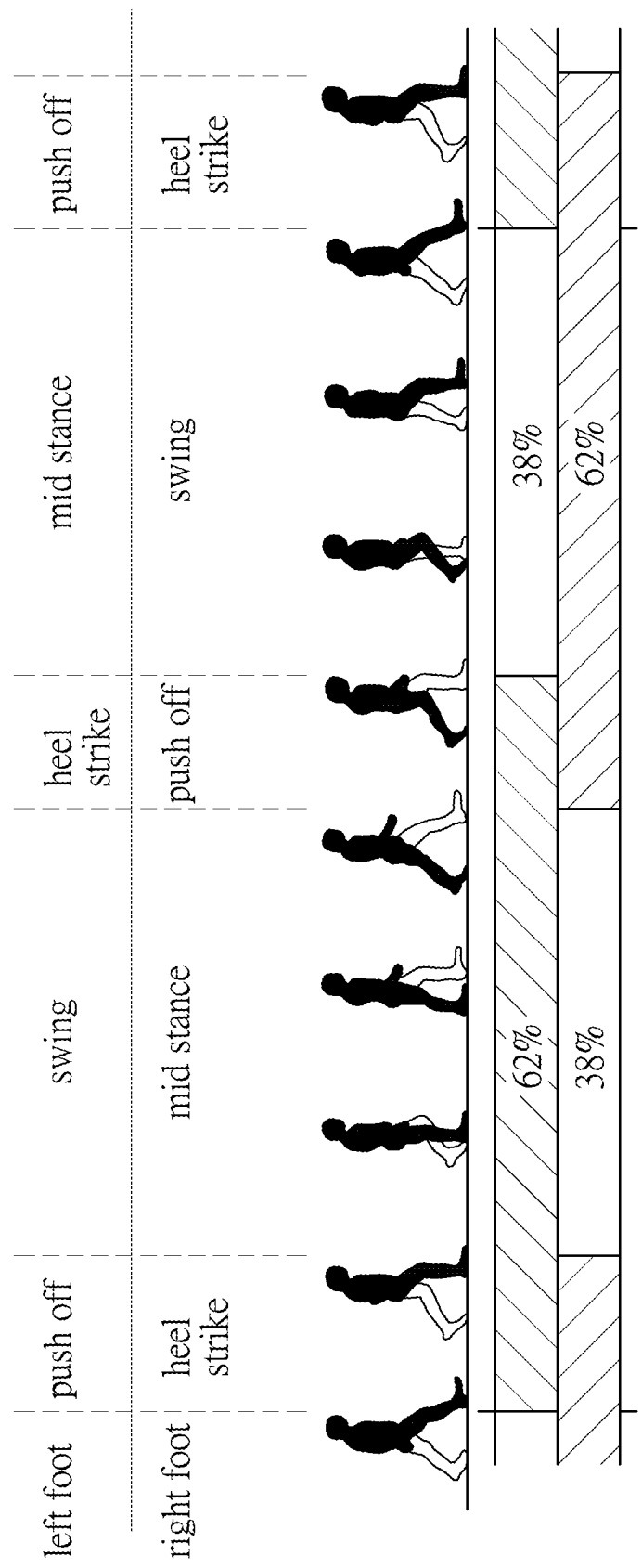
FIG. 3 is a schematic diagram illustrating respective gait cycles of two feet of a person who is walking.
Figure 4:
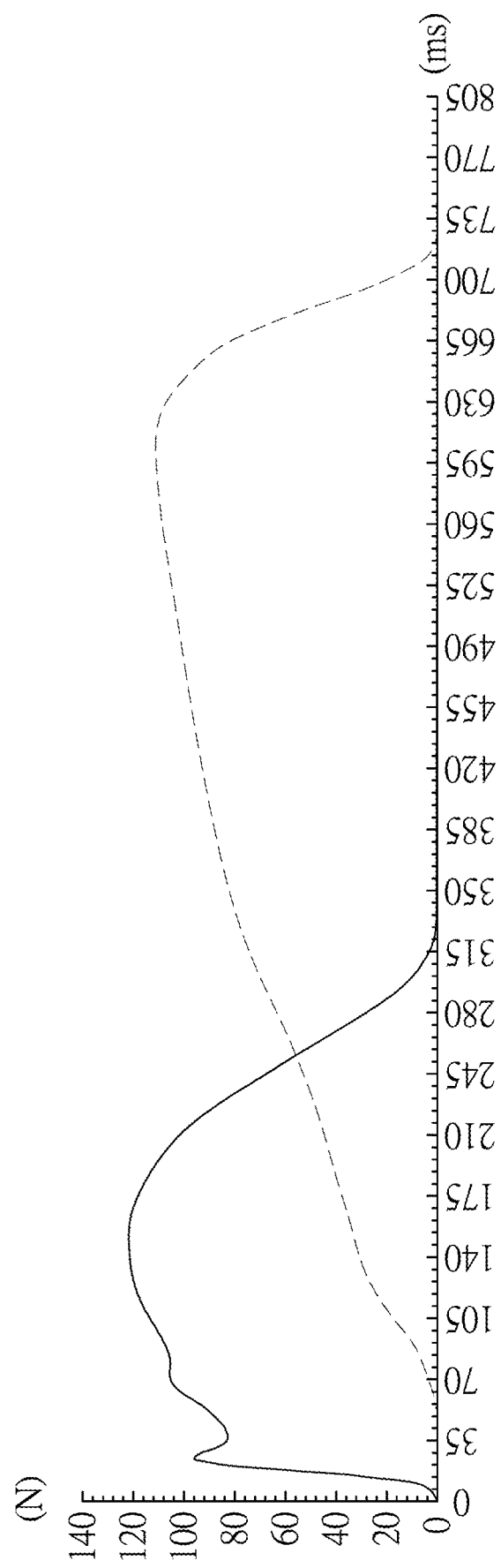
FIG. 4 is an exemplary timing diagram illustrating pressures sensed by the detecting module of the first embodiment.

When a person is walking, a gait cycle of each foot thereof can be divided into a heel strike phase, a mid stance phase, a push off phase and a swing phase as shown in FIG. 3. Meanwhile, if one of the shoes being worn by the person is mounted with the gait aid 100 of this embodiment, an example of the pressures respectively sensed by the first and second pressure sensors 21, 22 is shown in FIG. 4. In FIG. 4, the pressure sensed by the first pressure sensor 21 is depicted by a dashed line; the pressure sensed by the second pressure sensor 22 is depicted by a solid line; and the corresponding foot (i.e., the foot wearing the shoe 1 with the gait aid 100 mounted thereto) is in the heel strike phase during a time period from about 0 ms to about 70 ms, is in the mid stance phase during a time period from about 70 ms to about 315 ms, is in the push off phase during a time period from about 315 ms to about 720 ms, and is in the swing phase after about 720 ms.

Referring to FIGS. 1, 2 and 4, in this embodiment, the control circuit 4 further receives a predetermined first pressure value and a predetermined second pressure value from, for example, an external input device or an external memory, and generates the control signal based further on the predetermined first and second pressure values. The gait aid 100 is determined by the control circuit 4, based on the first sense signal and the predetermined first pressure value, to enter the projection state when the pressure sensed by the first pressure sensor 21 increases to become greater than the predetermined first pressure value (e.g., zero). The gait aid 100 is determined by the control circuit 4, based on the second sense signal and the predetermined second pressure value, to leave the projection state when the pressure sensed by the second pressure sensor 22 decreases to reach the predetermined second pressure value (e.g., zero). As a result, the cueing mark is projected when the foot in the shoe 1 is in the mid stance phase in this embodiment. It should be noted that the first and second pressure values may be determined based on personal conditions of a wearer of the shoe 1. In other embodiments, the control circuit 4 may further receive only one predetermined pressure value from, for example, an external input device or an external memory, and may generate the control signal based further on the predetermined pressure value. The gait aid 100 may be determined by the control circuit 4 to be in the projection state when the pressures respectively sensed by the first and second pressure sensors 21, 22 are both greater than the predetermined pressure value (e.g., zero), and to be not in the projection state when otherwise. As a result, the cueing mark is also projected when the foot in the shoe 1 is in the mid stance phase in the other embodiments. It should be noted that the predetermined pressure value may be determined based on personal conditions of a wearer of the shoe 1.

Figure 5:
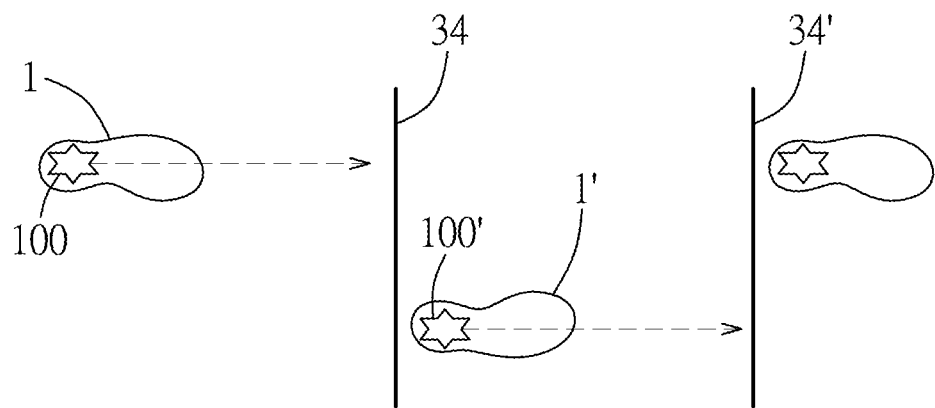
FIG. 5 is a schematic diagram illustrating a cueing mark projected by the first embodiment.

Referring to FIGS. 1, 2 and 5, under a circumstance where a person is performing gait training and is wearing a pair of the shoes 1, 1', when a left foot of the person is in the mid stance phase, the gait aid 100 disposed on the left shoe 1 projects the cueing mark 34, so as to advise the person to move a right foot thereof to a location indicated by the cueing mark 34 on the ground; and when the right foot of the person is in the mid stance phase, the gait aid 100' disposed on the right shoe 1' projects the cueing mark 34', so as to advise the person to move the left foot thereof to a location indicated by the cueing mark 34' on the ground. It should be noted that, when each cueing mark 34, 34' (e.g., the cueing mark 34) is directly in front of the corresponding shoe 1, 1' (e.g., the left shoe 1) on the ground, the person can practice walking in a straight line; and when each cueing mark 34, 34' (e.g., the cueing mark 34) is towards the right or left in front of the corresponding shoe 1, 1' (e.g., the left shoe 1) on the ground, the person can practice walking in a curved line. In addition, everyone has a step distance that is correlated to a leg length thereof. For example, an average step distance for adults is 69.5 cm, an average step distance for male adults is 74 cm, and an average step distance for female adults is 66 cm. For each gait aid 100, 100' (e.g., the gait aid 100), the angle of the projecting module 3 may be adjusted based on a step distance of the person such that the person is able to move the foot (e.g., the right foot) corresponding to the other gait aid 100, 100' (e.g., the gait aid 100') to the location indicated by the cueing mark 34, 34' (e.g., the cueing mark 34) on the ground. Moreover, when only one of the feet (e.g., the right foot) of the person requires gait training, the aperture of the mask 32 of the gait aid 100, 100' (e.g., the gait aid 100') corresponding to said one of the feet (e.g., the right foot) may be adjusted to be fully closed, so only the gait aid 100, 100' (e.g., the gait aid 100) corresponding to the other one of the feet (e.g., the left foot) can project the cueing mark 34, 34' (e.g., the cueing mark 34).

It should be noted that, in other embodiments, the following variations may be made:

1. The connection of the control circuit 4 to the detecting module 2 may be omitted, and the control circuit 4 may receive the sense output from the detecting module 2 in a wireless manner, instead of in a wired manner.

2. The control signal may play no role in the generation of the cueing mark by the light source 31, and the adjustor 33 may adjust the aperture of the mask 32 based on the control signal such that the passage of the cueing mark through the aperture is allowed (i.e., the cueing mark is not masked) when the gait aid 100 is determined to be in the projection state, and such that the passage of the cueing mark through the aperture is prevented (i.e., the cueing mark is masked) when the gait aid 100 is determined to be not in the projection state.

3. The mask 32 and the adjustor 33 may be omitted, so the intensity of the cueing mark 34 is not changeable.

Figure 6:
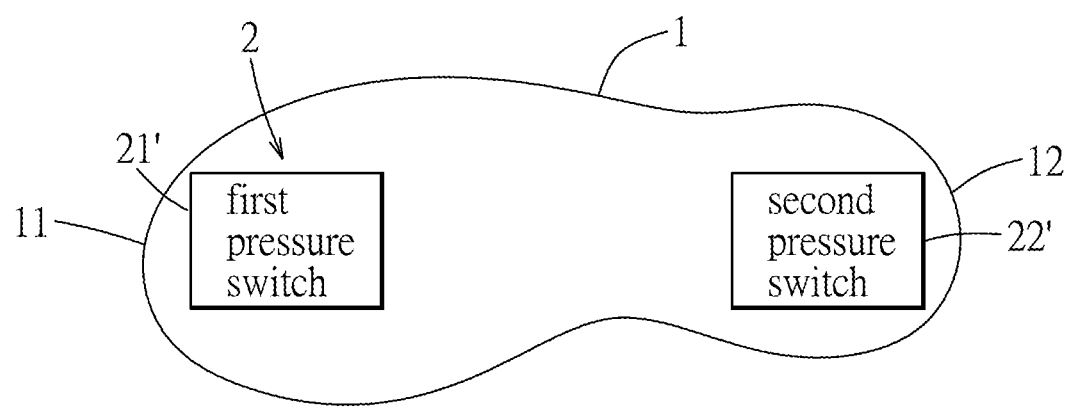
FIG. 6 is a schematic diagram illustrating the detecting module of a second embodiment of the gait aid according to the disclosure.

Referring to FIGS. 1 and 6, a second embodiment of the gait aid 100 according the disclosure is similar to the first embodiment, and differs from the first embodiment in that a first pressure switch 21' and a second pressure switch 22' are used to respectively replace the first and second pressure sensors 21, 22 (see FIG. 2), and in how the control circuit 4 operates.

In the second embodiment, each of the first and second pressure switches 21', 22' is operable between conduction and non-conduction based on the pressure exerted on the sole of the shoe 1, and respective operating states of the first and second pressure switches 21', 22' cooperatively serve as the sense output. For example, each of the first and second pressure switches 21', 22' conducts when the pressure associated therewith is relatively high, and does not conduct when the pressure associated therewith is relatively low.

In this embodiment, the predetermined first and second pressure values play no role in the generation of the control signal, and are not provided to the control circuit 4. The control circuit 4 stores information about the operating states of the first and second pressure switches 21', 22' in the memory module 7, and does not receive the predetermined first and second pressure values. The gait aid 100 is determined by the control circuit 4 to be in the projection state when the first and second pressure switches 21', 22' are detected to be both conducting, and to be not in the projection state when otherwise.

It should be noted that: (a) a condition in which the first pressure switch 21' does not conduct while the second pressure switch 22' conducts corresponds to the heel strike phase; (b) a condition in which the first and second pressure switches 21', 22' both conduct corresponds to the mid stance phase; (c) a condition in which the first pressure switch 21' conducts while the second pressure switch 22' does not conduct corresponds to the push off phase; and (d) a condition in which the first and second pressure switches 21', 22' both do not conduct corresponds to the swing phase. Therefore, the cueing mark is projected when the foot in the shoe 1 is in the mid stance phase in this embodiment.

Figure 7:
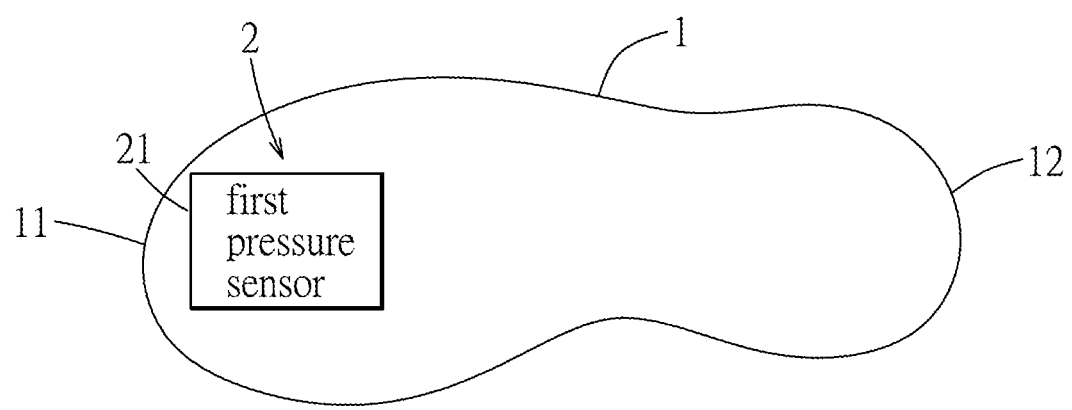
FIG. 7 is a schematic diagram illustrating the detecting module of a third embodiment of the gait aid according to the disclosure.

Referring to FIGS. 1 and 7, a third embodiment of the gait aid 100 according the disclosure is similar to the first embodiment, and differs from the first embodiment in that the second pressure sensor 22 (see FIG. 2) is omitted, and in how the control circuit 4 operates.

In the third embodiment, the first sense signal itself serves as the sense output. As no second pressure sensor 22 (see FIG. 2) is included in this embodiment, the control circuit 4 only stores the pressure sensed by the first pressure sensor 21 in the memory module 7. In addition, the predetermined second pressure value plays no role in the generation of the control signal, and the control circuit 4 does not receive the predetermined second pressure value. The gait aid 100 is determined by the control circuit 4, based on the first sense signal, to leave the projection state when the pressure sensed by the first pressure sensor 21 starts to decrease. Alternatively, the gait aid 100 may be determined by the control circuit 4, based on the first sense signal and a third pressure value (which is greater than the predetermined first pressure value), to leave the projection state when the pressure sensed by the first pressure sensor 21 increases to be above the third pressure value. In an example, the control circuit 4 further receives, from, for example, an external input device or an external memory, a predetermined constant that serves as the third pressure value. In another example, the control circuit 4 determines, based on the first sense signal, the third pressure value to be associated with a latest maximum of the pressure sensed by the first pressure sensor 21 (e.g., the third pressure value equals $(0.8 \Box Pmax)$, where Pmax denotes the latest maximum of the pressure sensed by the first pressure sensor 21). As a result, the projection of the cueing mark starts when the foot in the shoe 1 enters the mid stance phase, and may end before, at the moment when or after the foot in the shoe 1 leaves the mid stance phase in this embodiment. It should be noted that the constant may be determined based on personal conditions of a wearer of the shoe 1.

Referring to FIGS. 1, 2 and 7, in a modification of the gait aid 100 based on either the first or third embodiment (hereinafter referred to as the modified gait aid 100 for simplicity), the control circuit 4 may generate a communication output based on the sense output, and may wirelessly transmit the communication output. The communication output carries information about the pressures respectively sensed by the first and second pressure sensors 21, 22, or about the pressure sensed by the first pressure sensor 21 alone. The control circuit 4 may further wirelessly receive another communication output from another modified gait aid (which is identical to the modified gait aid 100, and which is to be disposed on another shoe paired with the shoe 1), and may generate the control signal based further on the received communication output. When determining, based at least on the sense output and the received communication output, that the modified gait aid 100 and the another modified gait aid are both in a projectable state (i.e., when a person who is wearing the shoe 1 and the another shoe is standing but not walking, and the feet thereof are in a freezing-of-gait phase), and that variation of the pressure exerted on the sole of the another shoe is greater than variation of the pressure exerted on the sole of the shoe 1(i.e., the person attempts to initiate a step from the foot in the another shoe), the modified gait aid 100 is determined by the control circuit 4 to be in the projection state. When determining, based at least on the sense output and the received communication output, that the modified gait aid 100 is in the projectable state while the another modified gait aid is not in the projectable state, the modified gait aid 100 is determined by the control circuit 4 to be in the projection state. Otherwise, the modified gait aid 100 is determined by the control circuit 4 to be not in the projection state. The modification of the gait aid 100 modified based on the first embodiment is determined by the control circuit 4 to enter the projectable state when the pressure sensed by the first pressure sensor 21 increases to be above the predetermined first pressure value, and is determined by the control circuit 4 to leave the projectable state when the pressure sensed by the second pressure sensor 22 decreases to reach the predetermined second pressure value. The modification of the gait aid 100 modified based on the third embodiment is determined by the control circuit 4 to enter the projectable state when the pressure sensed by the first pressure sensor 21 increases to be above the predetermined first pressure value, and is determined by the control circuit 4 to leave the projectable state when the pressure sensed by the first pressure sensor 21 starts to decrease or when the pressure sensed by the first pressure sensor 21 increases to be above the third pressure value. As a result, when the shoes worn by the two feet of the user are provided with the modified gait aids 100 of the same type (based either on the first embodiment or the third embodiment), at most one of the modified gait aids 100 projects the cueing mark at a time.

In view of the above, for each of the first to third embodiments and the modifications based on the first and third embodiments, since the gait aid 100 is to be disposed on the shoe 1 and is operable, based on the pressure exerted on the sole of the shoe 1, to project or not to project the cueing mark, the person who is wearing the shoe 1 can perform gait training without carrying anything extra. In addition, the gait aid 100 can detect the mid stance phase of the foot of the person in the shoe 1. Again, for each of the modifications based on the first and third embodiments, the gait aid 100 can detect the freezing-of-gait phase of the feet of the person, and can selectively project the cueing mark when the freezing-of-gait phase is detected.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that the disclosure is not limited to the disclosed embodiments but is intended to cover various arrangements included within the spirit and scope of the broadest interpretation so as to encompass all such modifications and equivalent arrangements.

What is claimed is:

1. A gait aid to be disposed on a shoe of a user, and operatively associated with an additional one of said gait aid, the additional one of said gait aid being disposed on another shoe of said user, and transmitting a communication output which is associated with pressure exerted on a sole of the another shoe, said gait aid comprising:
    a detecting module for continuously generating a sense output based on pressure exerted on a sole of the shoe;
    a control circuit used to receive the communication output from the additional one of said gait aid, and generating a control signal based at least on the sense output generated by said detecting module and the communication output; and
    a projecting module electrically coupled to said control circuit for receiving the control signal therefrom, and operable, based on the control signal, to project or not to project a cueing mark;
    wherein, when said control circuit determines, based on the sense output and the communication output, that said gait aid and the additional one of said gait aid both correspond to a mid-stance phase, and that the pressure exerted on the sole of the another shoe has greater amount of variation over time than the pressure exerted on the sole of the shoe, said gait aid operates in a projection mode, the mid-stance phase starting when toes of a foot contact ground and ending when a heel of the foot leaves ground;
    wherein, when said control circuit determines, based on the sense output and the communication output, that said gait aid corresponds to the mid-stance phase while the additional one of said gait aid does not correspond to the mid-stance phase, said gait aid operates in the projection mode;
    wherein, in the projection mode, said control circuit generates the control signal in such a way that said projecting module projects the cueing mark, and otherwise, said control circuit generates the control signal in such a way that said projecting module does not project the cueing mark.

2. The gait aid of claim 1, wherein said detecting module includes a pressure sensor that is to be disposed at a front portion of the shoe, and that senses the pressure exerted on the sole of the shoe to generate a sense signal that serves as the sense output.

3. The gait aid of claim 2, wherein said control circuit determines, based on the sense signal and a predetermined first pressure value, that said gait aid starts to correspond to the mid-stance phase when the pressure sensed by said pressure sensor increases to be above the predetermined first pressure value.

4. The gait aid of claim 3, wherein said control circuit determines, based on the sense signal, that said gait aid no longer corresponds to the mid-stance phase when the pressure sensed by said pressure sensor starts to decrease.

5. The gait aid of claim 3, wherein said control circuit determines, based on the sense signal and a second pressure value which is greater than the predetermined first pressure value, that said gait aid no longer corresponds to the mid-stance phase when the pressure sensed by said pressure sensor increases to be above the second pressure value.

6. The gait aid of claim 1, wherein said detecting module includes a first pressure sensor and a second pressure sensor that are to be disposed respectively at a front portion and a rear portion of the shoe, and that sense the pressure exerted on the sole of the shoe to respectively generate a first sense signal and a second sense signal which cooperatively serve as the sense output.

7. The gait aid of claim 6, wherein said control circuit determines, based on the first sense signal and a predetermined first pressure value, that said gait aid starts to correspond to the mid-stance phase when the pressure sensed by said first pressure sensor increases to be above the predetermined first pressure value.

8. The gait aid of claim 7, wherein said control circuit determines, based on the second sense signal and a predetermined second pressure value, that said gait aid no longer corresponds to the mid-stance phase when the pressure sensed by said second pressure sensor decreases to reach the predetermined second pressure value.

9. The gait aid of claim 6, wherein said control circuit determines, based on the first and second sense signals and a predetermined pressure value, that said gait aid corresponds to the mid-stance phase when the pressures respectively sensed by said first and second pressure sensors are both greater than the predetermined pressure value.

10. The gait aid of claim 1, wherein:
    said detecting module senses the pressure exerted on the sole of the shoe at a front portion of the shoe;
    said control circuit determines that said gait aid starts to correspond to the mid-stance phase when the pressure sensed by said detecting module increases to be above a predetermined first pressure value; and said control circuit determines that said gait aid no longer corresponds to the mid-stance phase when the pressure sensed by said detecting module starts to decrease or when the pressure sensed by said detecting module increases to be above a second pressure value greater than the predetermined first pressure value.

11. The gait aid of claim 1, wherein:

said detecting module senses the pressure exerted on the sole of the shoe at a front portion and a rear portion of the shoe;

said control circuit determines that said gait aid starts to correspond to the mid-stance phase when the pressure sensed by said detecting module at the front portion of the shoe increases to be above a predetermined first pressure value; and said control circuit determines that said gait aid no longer corresponds to the mid-stance phase when the pressure sensed by said detecting module at the rear portion of the shoe decreases to reach a predetermined second pressure value.

12. The gait aid of claim 1, wherein said control circuit determines, based on the sense output and the communication output, that said gait aid corresponds to a freezing-of-gait phase.

13. The gait aid of claim 12, wherein, when determining, based on the sense output and the communication output, that said gait aid and the additional one of said gait aid both correspond to the mid-stance phase, said control circuit determines that said gait aid corresponds to the freezing-of-gait phase.

* * * * *